United States Patent [19]

Gancet et al.

[11] Patent Number: 6,036,830
[45] Date of Patent: Mar. 14, 2000

[54] DESALINATION OF AQUEOUS SULPHONAMIDE SOLUTIONS

[75] Inventors: Christian Gancet; Didier Lauranson, both of Lons; Frederic Perie, Billere, all of France

[73] Assignee: Elf Atochem S.A., France

[21] Appl. No.: 09/172,172

[22] Filed: Oct. 14, 1998

[30]    Foreign Application Priority Data

Oct. 15, 1997 [FR] France .................................. 97 12901

[51] Int. Cl.⁷ .................................................. B01D 61/44
[52] U.S. Cl. ........................... 204/529; 204/530; 204/541
[58] Field of Search .................................... 204/529, 530, 204/541

[56]              References Cited

U.S. PATENT DOCUMENTS 5,145,569  9/1992  Schneider et al. ....................... 204/529
5,282,939  2/1994  Voss ......................................... 204/529
5,597,466  1/1997  Bauer et al. ............................. 204/529

FOREIGN PATENT DOCUMENTS

| 360093 | 4/1993 | European Pat. Off. . |
| 536021 | 4/1993 | European Pat. Off. . |
| 2708266 | 2/1995 | France . |
| 63-083058 | 4/1988 | Japan . |
| 7-080254 | 3/1995 | Japan . |

OTHER PUBLICATIONS

French Search Report dated Jul. 6, 1998.

*Primary Examiner*—Arwn S. Phasge

[57]           ABSTRACT

In order to remove the salts (in particular $NH_4Cl$) present in an aqueous sulphonamide solution (in particular $CH_3SO_2NH_2$), the solution is subjected to a two-compartment electrodialysis. By maintaining the pH at a value below 7, the formation of ammonia is avoided. The demineralized solution can be concentrated in order to receover after crystallization, the sulphonamide.

7 Claims, No Drawings

DESALINATION OF AQUEOUS SULPHONAMIDE SOLUTIONS

FIELD OF THE INVENTION

The present invention concerns the field of water-soluble sulphonamides and relates more particularly to a process for allowing the recovery and purification of sulphonamides obtained by an aqueous-phase synthetic process. The invention relates more especially to methanesulphonamide $CH_3SO_2NH_2$ (also referred to as MSAM), but more generally to all water-soluble sulphonamides.

BACKGROUND OF THE INVENTION

When sulphonamides are prepared in aqueous phase, an aqueous sulphonamide solution is finally obtained, which, in order to be able to isolate the sulphonamide, must be concentrated so as to crystallize the sulphonamide. Unfortunately, the aqueous solution to be concentrated generally contains salts, in particular ammonium chloride, which makes this concentration step difficult.

The prior art does not mention the use of membrane techniques in processes for the synthesis of sulphonamides, which, such as that of patent FR 2,708,266, use reactions carried out in a solvent medium such as acetonitrile or propionitrile.

The use of electrodialysis membranes to desalinate aqueous solutions is known to those skilled in the art and forms the subject, in particular, of patent EP 536,021, which relates to the desalination of aqueous solutions of polar aprotic solvents.

Application of this technique to the desalination of aqueous sulphonamide solutions derived from an aqueous-phase synthetic process is, however, unknown. Given that the sulphonamides concerned (in particular MSAM) have a relatively low molecular mass, they are liable to diffuse considerably across the membranes and it might be feared that high desalination yields could not be obtained.

DESCRIPTION OF THE INVENTION

It has now been found that the salts present in an aqueous sulphonamide solution can be removed with a high desalination yield by subjecting this solution to a two-compartment electrodialysis, provided that the solution is maintained at an acidic pH.

The salts (in particular $NH_4Cl$) pass from the solution (diluate) containing the sulphonamide to a receiver solution (concentrate) and, provided that the system remains at an acidic pH in order to avoid the diffusion of non-protonated ammonia, the removal of $NH_4Cl$ poses no problems.

The subject of the invention is thus a process for desalinating an aqueous sulphonamide solution, characterized in that this solution, maintained at an acidic pH, is subjected to a two-compartment electrodialysis.

In order to carry out the process according to the invention, commercial cationic and anionic ion-exchange membranes can be used, such as, for example, those sold by the company Asahi Glass under the name Selemion®, by the company Tokuyama Soda under the name Neosepta® or by the company Aqualytics. These commercial membranes generally have a thickness of between 0.1 and 1 mm and a pore diameter of between 1 and 30 μm. The ion-exchange membranes usually consist of a polymer matrix (for example polystyrene/divinylbenzene) onto which anionic groups (for example carboxylate or sulphonate) are chemically bonded for the cation-exchange resins, or cationic groups (for example substituted ammonium) for the anion-exchange resins. So-called "selective" membranes, with a narrower polymer structure, have been developed in order to retain di- and trivalent ions (sulphate, calcium, magnesium, etc.) and to allow monovalent ions (chloride, sodium, etc.) to pass through.

The sulphonamide concentration of the solution to be desalinated can vary within a wide range and is generally between 0.1 M and the solubility limit of the sulphonamide considered. This concentration is preferably between 0.5 and 2 M.

In accordance with the process according to the invention, the solution to be desalinated is maintained at an acidic pH, preferably between 2 and 6 and more particularly between 3 and 5. This can be done, for example, by addition of dilute HCl (0.05 to 0.5 M) to the saline solution. HCl is usually suitable, but depending on the anion of the salt to be removed, other monoacids can be used.

EXAMPLES

The examples which follow illustrate the invention without limiting it.

EXAMPLE 1

The solution to be treated was an equimolar mixture of methanesulphonamide (MSAM) and $NH_4Cl$ at pH 4.4. The receiver solution was a 5 g/l sodium chloride solution, as well as the electrolyte solution.

An SRTI electrodialyser of type P1 equipped with AMV and CMV standard membranes from Asahi Glass for a cell surface of 0.138 $m^2$ (for a two-compartment device, 1 $m^2$ of cell corresponds to 1 $m^2$ of cationic membrane+1 $m^2$ of anionic membrane, i.e. 2 $m^2$ of membranes) was used.

The current density applied was 435 $A/m^2$, except at the end of the test when the conductivity was too low; a voltage of 1.5 V per cell was then applied.

During the electrodialysis, the pH was maintained between 3 and 5 by addition of 0.1 M HCl so as to avoid any formation of ammonia which might diffuse and contaminate the MSAM produced.

The MSAM was analysed by gas chromatography. The ammonium chloride was monitored by conductimetry during the test and measured by ionic chromatography on samples taken.

The duration of the test was 0.66 hour. The roductivity of the device was 11.3 kg of 1 M MSAM solution treated per hour and per $m^2$, the energy consumed being 45.1 kWh per tonne of 1 M MSAM solution treated.

Table 1 below indicates the level of demineralization achieved on the MSAM solution after the electrodialysis treatment.

TABLE 1

| | CONCENTRATION (millimol/liters) | |
| --- | --- | --- |
| | initial | final |
| MSAM | 1000 | 880 |
| $NH_4Cl$ | 1000 | 2.9 |

Table 2 below indicates the salt and MSAM concentrations during the test, as well as the mass balance for the MSAM.

TABLE 2

|  | MSAM compartment (diluate) | Salt compartment (concentrate) |
|---|---|---|
| $NH_4Cl$ concentration (millimol/liter) | | |
| initial | 1000 | 85.5 |
| final | 2.9 | 1070 |
| MSAM concentration (millimol/liter) | | |
| initial | 1000 | 0 |
| final | 880 | 55 |
| Mass balance for MSAM (in g) | | |
| initial mass | 94 | 0 |
| final mass | 83.5 | 7.7 |

These results indicate that MSAM is correctly retained in the diluate compartment, the losses by passive diffusion being about 8.4% by weight. The yield observed is 91.6% by weight.

Depending on the target level of yield of MSAM, the final salt concentration can be adjusted by stopping the electrodialysis before depletion of the saline solution.

The final $NH_4Cl$ concentration is limited by the minimum conductivity to be conserved in order to allow the passage of current. In order to obtain more thorough levels of demineralization, the low conductivity of the solution can be compensated for by placing a resin or an ion-exchange felt pad in the salt compartment of the electrodialyser.

EXAMPLE 2

In order to treat an equimolar mixture of MSAM and $NH_4Cl$ at pH 4.15, the process was performed as in Example 1, but using ASV and CHV selective membranes from Asahi Glass.

The duration of the test was 0.7 hour. The productivity of the device was 10.1 kg of 1 M MSAM solution treated per hour and per $m^2$, the energy consumed being 45.8 kWh per tonne of 1 M MSAM solution treated.

Table 3 below indicates the level of demineralization achieved on the MSAM solution after the electrodialysis treatment.

TABLE 3

|  | CONCENTRATION (millmol/liters) | |
|---|---|---|
|  | initial | final |
| MSAM | 1000 | 845 |
| $NH_4Cl$ | 1000 | 0.6 |

Table 4 below indicates the salt and MSAM concentrations during the test, as well as the mass balance for MSAM.

TABLE 4

|  | MSAM compartment (diluate) | Salt compartment (concentrate) |
|---|---|---|
| $NH_4Cl$ concentration (millimol/liter) | | |
| initial | 1000 | 93.5 |
| final | 0.6 | 835 |
| MSAM concentration (millimol/liter) | | |
| initial | 1000 | 0 |
| final | 845 | 22 |
| Mass balance for MSAM (in g) | | |
| initial mass | 92.5 | 0 |
| final mass | 75.2 | 2.6 |

MSAM is correctly retained in the diluate compartment, the losses by passive diffusion being about 3.3% by weight. The yield observed is thus 96.7% by weight.

This example shows that the use of more selective membranes (with a narrower polymer structure) allows the level of loss of MSAM to be reduced from 8.4 to 3.3%.

We claim:

1. Process for desalination an aqueous sulphonamide solution, comprising subjecting this solution, maintained in an acidic pH, to a two-compartment electrodialysis.

2. Process according to claim 1, wherein the pH is maintained between 2 and 6.

3. Process according to claim 2, wherein the pH is between 3 and 5.

4. Process according to claim 1, wherein the acidic pH is maintained by addition of hydrochloric acid to the saline solution.

5. Process according to claim 1, wherein the sulphonamide concentration of the solution to be desalinated is between 0.1 M and its solubility limit in the saline solution.

6. Process according to claim 5, wherein the sulphonamide concentration is between 0.5 and 2 M.

7. Process according to claim 1, wherein the sulphonamide is methanesulphonamide.

* * * * *